(12) United States Patent
Coleman

(10) Patent No.: US 8,900,720 B2
(45) Date of Patent: Dec. 2, 2014

(54) MULTI-FUNCTIONAL WOOD PRESERVATIVES BASED ON A BORATE/FATTY ACID COMBINATION

(75) Inventor: Robert D. Coleman, Verona, WI (US)

(73) Assignee: Summerdale, Inc, Verona, WI (US)

( * ) Notice: Subject to any disclaimer, the term of this patent is extended or adjusted under 35 U.S.C. 154(b) by 358 days.

(21) Appl. No.: 13/222,419

(22) Filed: Aug. 31, 2011

(65) Prior Publication Data

US 2012/0225311 A1   Sep. 6, 2012

Related U.S. Application Data

(60) Provisional application No. 61/378,524, filed on Aug. 31, 2010.

(51) Int. Cl.
*B32B 21/04* (2006.01)
(52) U.S. Cl.
USPC ...... 428/537.1; 427/393; 252/397; 504/116.1
(58) Field of Classification Search
USPC .................. 428/537.1; 427/393; 252/397; 504/116.1
See application file for complete search history.

(56) References Cited

U.S. PATENT DOCUMENTS

| 6,821,631 | B2 * | 11/2004 | Grantham et al. | 428/453 |
| 7,741,244 | B2 * | 6/2010 | Coleman | 504/116.1 |
| 7,820,594 | B2 * | 10/2010 | Coleman | 504/116.1 |

OTHER PUBLICATIONS

Coleman, R.D., Yang, V.W., and Clausen, C.A., "Performance characteristics of boric acid (or DOT)—fatty acid formulations as mold inhibitors for wood products," pp. 1-15, Submitted Aug. 7, 2012 to IBB and US Forest Service, RP-673, Madison WI (in press).

Clausen, C.A. and Yang, V.W., "Multicomponent biocide systems protect wood from decay fungi, mold fungi, and termites for interior applications," pp. 1-9, Jun. 6, 2004, International Research Group on Wood Preservation, Stockholm, Sweden, IRG/WP04-30333.

Coleman, R.D. and Clausen, C.A., "Multifactorial Antimicrobial Wood Protectants," pp. 1-10, Nov. 30, 2008, International Research Group on Wood Preservation, Stockholm, Sweden, IRB/WP08-30484.

Clausen, C.A., Coleman, R.D., and Yang, V.W., "Fatty Acid-Based Formulations for Wood Protection against Mold and Sapstain," pp. 301-304, May 2010, Forest Products Journal 60(3).

Coleman, R.D., Yang V.W., et al., "Efficacy of Fatty Acid Chemistry: Candidate Mold and Decay Fungicides," pp. 287-297 +2, May 23-25, 2010, Proceedings of 106th Meeting American Wood Protection Association, vol. 106.

* cited by examiner

*Primary Examiner* — Leszek Kiliman

(57) ABSTRACT

Wood preservatives, methods for protecting wood and wood-based products and/or structures utilizing the preservatives, and treated wood and wood-based articles and/or structures incorporating the preservatives are described. Methods are also provided for remediating structures already infected with mold. The subject wood preservative formulation includes a borate compound and a fatty acid. The addition of an emulsifier to the formulation further facilitates application of the treatment. The combination of a borate compound and fatty acid combination typically provide a synergistic effect compared to the additive result provided by the combination's individual components.

16 Claims, No Drawings

MULTI-FUNCTIONAL WOOD PRESERVATIVES BASED ON A BORATE/FATTY ACID COMBINATION

CROSS-REFERENCES TO RELATED APPLICATIONS

This application claims the benefit of U.S. Provisional Patent Application No. 61/378,524, filed Aug. 31, 2010 and entitled MULTI-FUNCTIONAL WOOD PRESERVATIVES BASED ON A BORATE/FATTY ACID COMBINATION, which is incorporated herein by reference.

BACKGROUND

The Problem

Throughout recorded history wood and wood-based materials have provided an available and versatile construction material that can be cut, shaped, and fastened together to make a variety of useful structures. The life of such structures has generally depended on the builder's ability, the vagaries of nature, and the extent to which the structure was subject to damage by insects and decay. This application neither deals with the builder's skill or the vagaries of nature, but is concerned with providing sale and effective protection of treated wood and wood products from insect and fungal damage.

The early and current insecticides and fungicides utilized to protect wood from attack by insects and fungi are effective, but many can be toxic and unsuitable for use in modern homes sealed and insulated to reduce the exchange of hot or cold air from outside. In addition to concerns for exposure to insecticides and fungicides in modern homes, human health can also be adversely affected by mold contaminants, in addition to the wood preservatives meant to prevent wood disease such as mold and decay fungi. Humans are exposed constantly to molds in the environment, both indoors and outdoors. Problems arise when the immune system is suppressed (HIV infection, cancer treatment), over-responsive (allergy) or when exposures are exceedingly high (irritation and mycotoxin effects). Many people are allergic to molds, and allergic responses include hay fever and asthma. Certain molds such as *Stachybotrys chartarum* (or atra), and various species of *Avergillus, Fusarium* and *Penicillium* produce mycotoxins or volatile organic compounds (VOCs) that can be irritating when present in high concentrations and on occasion, can be quite toxic to humans and animals. Commonly, mold infestations and resulting health issues have been associated with building materials particularly wood and cellulose-based products. *Stachybotrys* is most commonly associated with very wet conditions (water activity level $a_w$ of 1.0) on cellulose products, such as the paper face of gypsum board, whereas *Penicillium, Aspergillus*, and *Cladisporium* sp. are associated with wood and wood products exposed to humidity conditions lower than saturation. Minimum water activity levels ($a_w$) are reported as 0.8 for *Aspergillus* and *Penicillium* or lower for some mold fungi.

Each year, billions of board feet of lumber are sold as unseasoned or green products and are allowed to dry naturally, usually during the framing stages of building a house. Mills can reduce the risk of mold and stain on green lumber by applying short term anti-stain or sap stain treatments which are thin coatings of fungicides on the wood surface. However, anti-sapstain treatments are usually reserved for select lumber products or wood destined for exportation. These fungicides are applied by dipping entire bundles of lumber into a treatment solution or by spraying all the primary surfaces of individual boards. Anti-sapstain chemicals, such as NP-1, are designed to provide a microscopic barrier against fungal attack that lasts for three to six months, depending on the chemical, the concentration used, the wood species and the climatic conditions. Because these fungicide treatments are not designed for long-term protection of wood products, mold infestation can readily occur if moisture is reintroduced beyond the period of time the treatment is effective.

Because of the recent increase in mold mitigation claims, as well as increased public awareness about indoor air quality (IAQ), the need for improved protection of cellulose-based building materials from mold infestations has been hastened. Mold claims, including pre- and post-construction, exceeded $3.0 billion in the U.S. in 2002, more than double the $1.3 billion paid in the previous year. While mold fungi do not cause structural damage to wood, the presence of mold is indicative of inadequate surface drying of condensation, chronic high humidity, or water intrusion. Chronic moisture issues can result in structural damage which often begins with growth of mold fungi followed by presence of decay fungi (i.e., brown-rot and white-rot fungi). Eventually, chronic moisture problems and decayed wood can attract other pests such as termites.

Spores from mold fungi can be particularly problematic not only as human and animal allergens but also due to their recalcitrance to chemical remediation. Among the three primary wood infestations (termite attack, mold and decay fungi), spores from mold fungi appear to be the most resistant to chemical treatments; hence, mold spores are more difficult to suppress and control. Excess moisture in existing structures can be caused by a number of factors including, but not limited to, flawed design, poor construction practices or maintenance, poor site drainage, leaky roofs/plumbing, inadequate insulation, improper ventilation, etc.

Regardless of how meticulous the maintenance on a building is, nearly every structure will encounter a moisture event that may be as obvious as flooding or as subtle as a chronic leak inside a wall that only becomes apparent in advanced stages of biological activity. Because even the best moisture management practices cannot prevent eventual moisture intrusion, economical biocides that are suitable for interior use are needed. In addition to being effective against mold fungi, they must be nontoxic to occupants, nonvolatile, environmentally acceptable, safe to handle, and possess low water solubility.

Surface treatment of dimension lumber or engineered products with mold inhibitors would add an additional layer of protection for in-service wood products and lessen the impact of current indoor air quality issues. This strategy is being used to some degree in the manufacture of gypsum board and oriented strand board. Clausen and Yang (2003) evaluated acids, phenolic compounds (antioxidants), pharmaceuticals, bio-preservatives, wood preservatives, food preservatives, and plant extractives for mold inhibitory properties.

Early and Current Solutions

Wood preservation for protection of home and other structures in the United States dates as early as the 17$^{th}$ century. Since then and even more recently, a key driver in the evolution of new wood preservatives replacing existing products is human health. Public perception related to product safety for citizens and the environment has greatly influenced state and federal policy decisions and in turn, industry's impetus to develop alternate products.

In the early 1700s use of mercuric chloride began, leading to coal-tar creosote in the mid-1800s and in the 940s, the development of chromated copper arsenate (CCA). Arsenic and hexavalent chromium, components of CCA, are recognized as known human carcinogens. Hexavalent chromium is classified as a human carcinogen based on excess lung cancer found in heavily exposed workers through inhalation in chromium plating and chromate and chromate pigment production. The literature is abundant with evidence of carcinogenicity for both arsenic and chromium. Due to societal perception together with increased technology development, product evolution towards safer choices for mold, decay and termite protection has accelerated over the last half century and probably more so in the last 10 years.

Nearly 60 years ago, Forest Products Laboratory (FPL) in Madison characterized ideal properties for a good wood preservative. Although the list has expanded, fundamentals given in the 1950s remain the same: 1) "poisonous to wood-destroying fungi", 2) "able to penetrate wood thoroughly", 3) "cost, availability and uniformity will largely determine its usefulness", 4) non-corrosive to metal and 5) "must not be a dangerous poison to men and animals"; the latter criteria has received more recent attention and hence, prompted changes in the wood preservation industry.

Public concern over leaching of arsenic from CCA-treated wood into waterways finally resulted in its virtual elimination by the US EPA (US Environmental Protection Agency) for residential uses such as decks, picnic tables, fencing, patios, play-structures, etc. . . . . According to industry observers, CCA production has dropped by 80% since 2003 and been replaced by ammoniacal copper quat ACQ and copper azole CA, Hingston, J. A. (2001) and other researchers provided scientific evidence that leachate bioaccumulation and toxicity could produce a significant source of metals in the aquatic environment. Currently, CCA applications in the U.S. are limited; primarily on marine pilings, telephone poles, railroad ties, etc. Nevertheless, CCA continues to be used in substantial volumes. For example, nearly 600 million cubic feet of wood poles (~4 million poles) are treated each year, a continuing concern per leaching of copper and arsenic as well as the issue of pole disposal. In most other major, industrialized countries, CCA use is severely restricted.

A search for arsenic-free products has been initiated by the major wood preservative manufacturers. New copper-based systems emerged, combining salts or oxides of copper and sometimes, zinc, iron, aluminum or boron with various organic, active ingredients used as fungicides in agriculture. Ammoniacal copper quat or alkaline copper quaternary ammonium compounds (ACQ-A, B, C), amine copper qua (ACQ-D), and copper azole (CA) such as copper boron azole-Type A (CBA-A) were touted as lower toxicity preservatives relative to CCA and were standardized by the American Wood Protection Association (AWPA). ACQ-A was deleted in 2000 due to lack of use. Although performance in many cases matched CCA, cost of ACQ, for example, was much higher than CCA and more corrosive on metal.

Due to high aquatic toxicity, cost, corrosivity and other issues, the copper-based generation of new preservatives has experienced environmental pressure in certain areas of the world (Freeman, M. II., et al. 2003, Evans, P. 2003). Although copper preservatives are viewed as the probable dominant water-based treatments for the near term, many believe that all-organic biocides composed of safer fungicide (organic) moieties will represent the next generation of products (Freeman, M. et al. 2003, Evans, P. 2003). Evans (2003) mentions ongoing interest in use of natural active compounds such as salicylic acid, cypress pine oil and plant alkaloids (i.e., Neem tree extract). Yang (2006), after screening seven essential oils as candidate moldicides, found that thyme and geranium Egyptian oil inhibited all test fungi for 22 weeks. Several European countries may require totally organic 3rd generation systems where non-metallic preservatives for residential applications may eventually be mandated in the United States (Schultz, T. P. and D. D. Nicholas. 2003).

Problems with Current Solutions

The existing issues with copper-organic preservatives are summarized below.
  More expensive than CCA
  Fungal resistance and tolerance to copper by decay fungi
  Potential leaching of copper-organics: loss of preservative to environment, landfill issues
  Aquatic toxicity of copper at higher concentrations
  Acute and chronic toxicities of many current organic fungicides in copper-based preservatives
  Corrosion issues for fasteners and other metallic objects in contact with copper-based preservatives
  Biocide depletion
  Higher Costs: $2^{nd}$ generation ammoniacal/amine copper systems cost 2-4 times more than CCA. A copper-based preservative's organic biocide component, adopted from agricultural fungicides, can be 10-30 fold more expensive per pound than inorganic preservatives.

Resistance/Tolerance: Unlike other microbes, fungi (several brown-rot decay fungi) can be extremely tolerant of toxic metals at high concentrations using a diverse array of cellular mechanisms to acclimate to copper. For example, copper's biological availability can be reduced via complex of copper by fungal proteins and/or precipitation of copper as copper oxalate Copper and Organic Fungicide Leachates: A limiting feature of copper-rich biocides such as amine-copper preservatives is their leachability where up to 35% of copper can be lost (Waldron et al. 2003). Copper levels in ACQ and CA-B are several times higher than in CCA. Moreover, the newer copper biocides do not have an oxidant (as does CCA) to facilitate copper fixation in wood.

An important study by Dubey (2006) determined potential groundwater contamination from deck runoffs into soil columns and compared risk factors of various preservative leachates in different soil types. Alkaline copper quaternary ammonium (ACQ), compared to CCA, had almost 10 times higher chance of exceeding soil cleanup target level for copper. That is, copper concentrations in the CCA deck runoff samples were about 10-fold less than concentrations measured from ACQ-treated wood (Dubey, 2006).

In 2006, a micronized (micrometer-size pieces of copper) copper quat product (MCQ) was introduced which was reported to lessen copper leaching compared to soluble copper used in ACQ made by Viance and others. Copper preservatives used in North America may have limitations on use and even greater restrictions are expected on use and disposal in the future.

Aquatic Toxicity by Copper and Organic Biocides: Restriction of copper use in agriculture is based on the environmental impact caused by using large amounts of copper to obtain sufficient pathogen control. Because copper and sulfur compounds are not as effective as synthetic fungicides, overuse can be common, raising environmental concerns. Similar issues can exist with high amounts of copper applied as wood preservatives where metal leachates can potentially reach streams and rivers. Copper has very high aquatic toxicity and can also affect algae and plant life. Because of copper's potential to leach from treated wood and copper's aquatic toxicity, and other mentioned issues, a search for replacements for copper-based preservatives is underway.

Organic biocides applied as wood preservatives such as DDAC and other fungicides (chlorothalonil, propiconazole and 3-Iodo-2-propynyl butyl carbamate or IPBC) are also highly toxic to aquatic organisms including zooplankton and fish. DDAC and azole compounds are formulated with copper to prepare copper quats and azole preservatives. IPBC, propiconazole, tebuconazole and chlorothalonil are recognized as known or probable groundwater contaminants while chlorothalonil, tebuconazole and propiconazole have issues as chronic toxins; i.e., probable or possible carcinogens.

Human and Animal Toxicity of Fungicide Organics: Certain agricultural fungicides, combined with copper compounds (or other active ingredients) used as wood preservatives, are toxic, synthetic chemicals. A majority of the agricultural fungicides have high chronic toxicity, with some suspected as human carcinogens and others, toxic to birds, fish and beneficial insects, Chlorothalonil, IPBC and DDAC have high acute toxicity. As mentioned earlier. DDAC and other organic fungicides such as chlorothalonil, tebuconazole, propiconazole and IPBC are highly toxic to numerous aquatic organisms. Some of these fungicides may not be re-registered or their use severely restricted under the Food Quality Protection Act. Selected fungicide products have been given the highest priority for tolerance reassessment by the EPA.

The recently enacted Endocrine Disruptor Screening Program or EDSP examines potential effects of pesticide chemicals on the endocrine system and may eliminate use of selected fungicides. Congress, influenced by compelling evidence that endocrine systems of wildlife are affected by chemical contaminants, required the EPA initiate EDSP. Propiconazole, tebuconazole and chlorothalonil, as active ingredients, are on the EPA's Final List of Tier 1 trials for immediate testing and review. All three fungicides are currently used in wood preservative products as "next generation preservatives" replacing CCA. Azole compounds such as propiconazole and tebuconazole were already suspected to be endocrine disruptors. If EDSP Tier 1 and 2 trials show that a pesticide is problematic, the pesticide product (s), whether as a pesticide for plant protection or as a wood preservative, could be severely restricted in use or its registration revoked. Nearly all fungicides are synthetic compounds manufactured from petroleum precursors. The development of new and effective pesticides obtained from renewable feed-stocks rather than from petrochemicals is in the public interest.

Enhanced Corrosion by Copper Preservatives: Replacement of CCA with copper-based formulations such as alkaline copper quaternary (ACQ), ammoniacal copper zinc arsenate (ACZA) and copper azoles (CA) can corrode nails, screws and other metal fasteners especially in residential applications. ACQ, ACZA and CA are reported to be more corrosive to galvanic metal connectors than CCA.

Biocide Depletion: Photolytic and bacterial degradation of copper-based preservatives is well-known. Whereas azoles such as tebuconazole and propiconazole are attacked by a number of bacterial and fungal strains, *Pseudomonas* species are known to readily degrade QACs, IPBC and chlorothalonil. Metals often required by bacterial or fungal oxidation of organic biocides could possibly be bound or sequestered using natural chelators such as phytic acid or oligomers of polylactic acid (PLA). PLA is easily prepared by self-condensation of lactic acid monomers in a concentrated solution (>95%, g/v) using rotary evaporation. Phytic acid, a natural constituent of many plants and animals, is known to function in phosphate metabolism and can efficiently chelate heavy metals.

Current Needs:

What is needed is a replacement of copper-based preservatives such as alkaline copper quaternary ammonium compounds or ACQ and copper azoles (CA) (Evans, P. 2003, Freeman, M. H., et al. 2003). Protection against insect infestations such as termites and carpenter ants is similarly important for a suitable wood preservative. Formosan termite is estimated at a >$2 billion problem in southern coastal areas of the U.S. A wood preservative replacement should protect against damage from both microbes and insects. Most professionals expect that totally-organic preservatives for U.S. residential applications will be required in the near future. Preferred preservatives will be derived from non-petroleum sources. A suitable wood preservative should, in addition to protecting wood and wood-based products from insect and fungal attack (both rotting fungi and mold fungi), be safe to human and animal health and not contaminate the environment during a structure's useful life or after disposal. In order to be useful for indoor and outdoor construction, such a wood preservative must resist leaching when exposed to repeated contact with water. The present disclosure addresses these needs.

References

Clausen, C. A. and F. Green. 2003. Oxalic Overproduction by Copper-Tolerant Brown-rot Basidiomycetes on Southern Yellow Pine Treated with Copper-based Preservatives. International Biodeterioration & Biodegradation. 51 (2): 139-144, Duhey, B. Townsend, T. and H. Solo-Gabriele. 2006 Comparison of Relative Risks from Preservative Components in Soil Below Structures Made of CCA-, ACQ-, CBA- and DOT (Envirosafe)-Treated Wood. Wood Protection 2006. M. H. Barnes, Ed. Forest Products Society, Madison, Wis. Page 235-246.

Evans, P. 2003. Emerging Technologies in Wood Protection. Forest Products Journal. 53:1.

Freeman, M. H.; Shupe, Todd F.; Vlosky, Richard P.; Barnes, H. M.: 2003. Past, Present and Future of the Wood Preservation Industry: Wood is a Renewable Natural Resource that Typically is Preservative Treated to Ensure Structural Integrity in Many Exterior Applications. Forest Products Journal. Oct. 1, 2003.

Hingston, J. A., Collins, C. D., Murphy, R. J. and J. N. Lester. 2001. Leaching of Chromated Copper Arsenate Wood Preservatives: A Review. Environmental Pollution. Vol 111, issue 1, January 2001. Pages 53-66.

Schultz, T. P. and D. D. Nicholas. 2003, A Brief Overview of Non-Arsenical Wood Preservative Systems. (chapter 26, 420-432). In: Wood Deterioration and Preservation; Advances in our Changing World. (B. Goodell, D. D. Nicholas, and T. P. Schultz, Editors.) ACS, Washington, D.C.

Waldron, Y. T., Ung, Y. T. And P. A. Cooper, 2003. Leaching of Inorganic Wood Preservatives-Investigating the Relationship Between Leachability, Dissociation Characteristics and Long-term Leaching Potentials. Doe. No. IRG/WP 03-50199. 34th Annual Meeting of International Research Group on Wood Preservation.

Yang, V. and C. A. Clausen. 2006. Screening of Antifungal Activities of Essential Oils on Wood. Wood Protection 2006. NI. H. Barnes, Ed. Forest Products Society, Madison, Wis. Page 384.

SUMMARY

As will become apparent from the following discussion, the present disclosure provides compositions capable of protecting wood and wood-based materials from damage caused by insects, decay fungi, and mold fungi. The compositions are effective for interior and exterior applications, including applications with periodic or continuing exposure to water. In addition, methods for the incorporation of the compositions into wood or a wood-based product are described. Finally, treated wood-based articles are described which are capable of resisting damage caused by insects, decay fungi, and mold fungi. The treated wood-based articles do not include toxic materials and can be utilized for interior and exterior applications.

As used herein, the following terms have the meanings described below. A borate compound refers to a compound containing boron oxoanions or substituted boron oxoanions. Examples of borates include, but are not limited to salts of oxoanions such as for example, disodium octaborate tetrahydrate (DOT), boric acid, and a boronic acid (such as phenyl boronics). A fatty acid includes a carboxylic acid having between 5 and 22 carbon atoms. Additional borate salts which can be incorporated with fatty acids include, but are not limited to, zinc borate, sodium tetraborate, disodium tetraborate, calcium metaborate, borate esters (such as with 1,2 or 1,3 diols or 1, 3,5 triols). Fatty acids can be utilized in their acid form or as a salt. The ammonium salt of fatty acids is a particularly useful fatty acid salt.

A wood product or wood article refers to a product made with wood or that includes wood or a wood-derived product such as cellulose or a product containing cellulose. A wood product can be constructed of substantial material that is not a wood product or otherwise derived from wood, provided at least a portion of the product is wood-based or wood-derived. One example of such a wood-based or wood-derived product is gypsum board, primarily constructed from gypsum, but having a cellulose outer layer.

A first aspect of the present disclosure involves a composition that protects wood products and wood-based products against insects, decay fungi, and mold fungi in both interior and exterior applications. The composition is particularly useful in protecting treated wood products and wood-based products which are subject to repeated contact with water. The composition includes a borate compound, a fatty acid, and an emulsifier, where for the relationship between the amounts of borate compound and fatty acid is defined by the ratio of [borate compound]:[fatty acid] and the ratio can range from about 1:1000 to about 1000:1, For preferred compositions the ratio ranges front about 1:25 to about 10:1. For more preferred compositions the ratio ranges from about 1:15 to about 8:1. Finally, for the most preferred compositions, the ratio ranges from about 1:5 to about 4:1.

A further aspect of the present disclosure involves compositions which are capable of protecting wood products against insects, decay fungi, and mold fungi in interior and exterior applications and which include a borate compound, a fatty acid, and an emulsifier. For these compositions, the borate compound is selected from the group consisting of DOT, boric acid, a boronic acid, and combinations thereof.

A still further aspect of the present disclosure involves a method for protecting wood or a wood product from insects, decay fungi, and mold fungi. The method involves the steps of: (a) providing a wood product; (b) providing a borate compound; (c) providing a fatty acid; and (c) incorporating the borate compound and the fatty acid into the wood product. The step of incorporating can involve contacting the wood product with one or more formulations containing the borate and the fatty acid in a process involving soaking, dipping, brushing, spraying, diffusion, injection, vacuum, vacuum/pressure treatments or by painting or application of a coating material containing the fatty acid and borate compound. In addition, incorporating can include the inclusion of the composition into a wood-based article or wood composite such as particle board or oriented strand board during the article's manufacture. The incorporating step can be carried out at reduced pressure, atmospheric pressure, or at elevated pressure. For preferred methods, providing a borate compound involves providing a compound selected from the group consisting of DOT, boric acid, a boronic acid, and a combination thereof. Additionally, for further preferred methods, providing a fatty acid involves providing a compound selected from the group of caprylic acid, capric acid, heptanoic acid, pelargonic acid, and a combination thereof.

A still further aspect of the present disclosure involves a wood-based article including a borate compound and a fatty acid, included for preservation purposes; the treated article being capable of resisting attack by insects, decay fungi, and mold fungi. Preferred wood-based articles include a borate compound selected from the group consisting of DOT, boric acid, a boronic acid and a combination thereof. Such treated articles are capable of resisting attack in a wet environment after repeated exposures to water. Such preferred treated articles can additionally include a fatty acid selected from the group consisting of caprylic acid, capric acid, pelargonic acid, heptanoic acid and a combination thereof.

The combination of a borate and fatty acid can be applied as a remedial, restorative treatment solution for wood structures or wood composites contaminated with wood disease. Specifically, the remedial solution can be used as a rinse, spray, dip, brush or other application to inhibit, suppress and/or kill a) mold and decay fungi and their spores and/or b) insects such as termites and carpenter ants.

Other components can be added to the formulations described above to enhance one or more efficacies. For example, further moldicide enhancement can be obtained with the addition of one or more essential oils selected from the group consisting of thyme, camphor, clove, orange, geranium and dill weed.

Finally, a further aspect of the present disclosure includes a composition that includes a fatty acid, sorbic acid and an emulsifier. The composition, with or without the addition of a borate compound, has fungicidal properties and insecticidal properties and is useful for preserving a wood based article.

DESCRIPTION

For the purposes of promoting an understanding of the present disclosure, references will now be made to the embodiments illustrated and specific language will be used to describe the same. It will nevertheless be understood that no limitation of the scope of what is claimed is thereby intended, such alterations and further modifications and such further applications of the principles thereof as illustrated therein being contemplated as would normally occur to one skilled in the art to which the disclosure relates.

Certain borates are readily available, well known, and naturally occurring salts mined in saline deposits from Death Valley and Chile and have been used for decades as laundry additives and as a natural insecticide. Borate treated wood was initially developed in New Zealand, to resist insect damage. Borate treated wood entered the U.S. (mid-1990s) due to the success of disodium octaborate tetrahydrate (DOT)-pressure treated wood in Hawaii for controlling termites. After decades of use in Hawaii, borate treatments, under highly demanding test conditions, were found to be effective against decay fungi and wood destroying insects in indoor residential applications. Moreover, insects do not appear to have tolerance or develop resistance to borate.

The use of DOT for treating wood is now worldwide. The U.S., Australia and South Africa borates are commonly used for timber framed constructions. The natural mineral has a superb record of human (extremely low mammalian toxicity) and aquatic safety, is very inexpensive and does not corrode metal (Schultz, T. P. and D. D. Nicholas. 2003). DOT is relatively soluble in water and hence, has good penetration of all major structural lumber species in the U.S. Moreover, DOT treatments are compliant with major building codes and as is the case for borate compounds, non-corrosive to most metal nails, screws and fasteners.

However, borate leaching can occur with exposure to water, thus restricting the bulk of current borate treatments to indoor construction. As a result, borate treated lumber exposed to rainfall (leaching conditions) over time loses substantial amounts of the borate, reducing its effectiveness as a preservative. In addition, although DOT has demonstrated capability in combating insects and decay fungi, it has very limited function as a moldicide. In addition, current efforts to fix borates into a wood article have often resulted in a toss of activity.

In contrast, the present disclosure discloses specific formulations containing a fatty acid/borate combination that surprisingly provides excellent protection against insect damage, decay fungi and mold fungi for both leached and un-leached southern yellow pine. In addition, the combination's effectiveness is surprisingly greater than the additive effect of a fatty acid and a borate and the combination surprisingly resists leaching when exposed to an outdoor environment in which the treated wood product is repeatedly exposed to water. Suitable treatment methods include all conventional methods of treatment including, but not limited to, both dip and pressure treatment. Wood products and composites such as plywood, hardwood, oriented strand board, ceiling tile and wallboard treated in this manner resist attack by mold and decay fungi as well insect infestation.

One aspect of the present disclosure involves multi-functional fatty acid/borate combinations effective against insects and target wood disease pathogens. Surprisingly, the fatty acid/borate combination is substantially retained in the treated wood and/or cellulose containing product. That is, sufficient amounts of fatty acid/borate, as active ingredients for control of wood disease, remain in treated wood after repeated and prolonged exposure to water. Leached and unleached wood containing the fatty acid/borate combination has substantially the same insecticidal/fungicidal activity as an unleached wood sample making the combination suitable for exterior residential applications having repeated contact with water. The fatty acid/borate combination provides cost effective and safe performance required by the construction industry and the public's environmental and health concerns. Finally, in providing superior performance, the fatty acid/borate combinations exhibit an unexpected synergistic effect beyond any expected additive effects.

The formulation's components can be introduced into a wood product or a wood-derived product in serial fashion or combined into a single formulation incorporated in a single step, or can be physically incorporated into wood-based materials during manufacture. Methods of treatment can involve any known manner of incorporation and specifically can involve soaking, dipping, brushing, spraying, diffusion, injection, vacuum or vacuum/pressure treatments. The treatment method can be carried out at reduced pressure, atmospheric pressure, or at elevated pressure.

EXAMPLES

The examples which follow are illustrative and are not intended to limit the use or method of application for the novel compositions.

Example 1

Two treatments solutions were prepared for testing against termites. The first treatment solution was an emulsion including 2% C-9 (pelargonic acid), 0.056% unmodified lecithin #750, 0.18% boric acid, 0.08% copper gluconate, 0.034% SDS, and 1.52% glycerol (Table 1, treatment 1-1). The second treatment solution (treatment (1-3) contained 0.18% (g/v) of boric acid and 1.52% glycerol. Both solutions contained the same percent amounts of boric acid and glycerol. Blocks were treated (5 block replicates) with the two solutions. Following treatment, the treated blocks and untreated blocks were subjected to a no-choice test against termites (AWPA Standard E1-09, 2009*). The test results illustrated below in Table 1 illustrate that a C-9 (pelargonic acid)/boric acid formulation (1-1), caused 100% termite morbidity and only a 1.4% loss of block weight at 28 days. The second formulation (1-3) evaluated effects of only boric acid at 0.18% (g/v) in glycerol. Morbidity and block weight loss was 49.8 and 7.6%, respectively, at 28 days. The combination containing C-9 and boric acid (1-1) provided increased termiticidal activity over 0.18% boric acid, alone (1-3). Untreated or control blocks (1-2, 1-4) provided only coincidental termite mortality and weight losses ranging from 16-25%.

TABLE 1

Termiticide Assay*

| Composition | Termite Mortality (%)** (Days after infestation) | | | Weight Loss of Treated Blocks** (Days after infestation) |
|---|---|---|---|---|
| Treatments: | 6-7 | 11-12 | 28 | 28 |
| 1-1 C-9 formulation with glycerol/boric acid (solution #1) | 5.5 | 86 | 100 | 1.4 |
| 1-2 Control (untreated) | 0 | 0 | 3.5 | 16 |
| 1-3 Glycerol/boric acid (solution # 2) | 4 | 29 | 49.8 | 7.6 |
| 1-4 Control (untreated) | 0 | 0 | 1.5 | 24.8 |

*American Wood Protection Association. 2009. Standard Method for Laboratory Evaluation to Determine Resistance to Subterranean Termites E1-09. In: American Wood Protection Association Book of Standards. Birmingham, Alabama, pp. 347-355.
**Termite mortality, weight loss: expressed as averages (%) based on 5 replicate blocks/treatment

Example 2

A stock formulation ("C8 only") was prepared containing 50% C8, 20% PE 1198 (a phosphate ester emulsifier available from Huntsman Chemical), 10% L-lactic, 20% mineral oil. Samples of the stock solution were diluted with water to provide a testing formulation having 8% stock formulation, v/v, in water. A disodium octaborate tetrahydrate or DOT solution ("DOT only") was prepared having 5% DOT g/v in water. A mixed formulation ("DOT+C8 combo") was prepared from the C8 only formulation with the addition of 5% DOT g/v (2-5, 2-9). Each test involved 10 replicate southern pine stakes utilizing 30 second dip treatments. Treatments 2-4 and 2-8 involved two-step treatments having a 4 hour drying period after the DOT treatment and before the CS treatment. The moldicide ratings provided in Table 2 were based on ratings wherein ratings of 1, 2, 3, 4 and 5 represented 20, 40, 60, 80 and 100% infection, respectively. The FPLSD: Fisher's Protected Least Significant Difference Ratings values with the same letters are not significant at P<0.05. Formulations containing both C8 and DOT were more effective in preventing mold than the components alone. The inclusion of a drying step between treatments further improved the combination's moldicide activity. All moldicide assays were conducted via ASTM standard D4445-91 (1998) and ASTM D3273-00 (1986).

TABLE 2

Moldicide Assay

| Test # | Non-Leached or Leached prior to testing | Formulation | Ratings after 8 weeks incubation Average | *FPLSD P @ 0.05 | Ratings after combined 4 and 8 week incubation Average | *FPLSD P @ 0.05 |
|---|---|---|---|---|---|---|
| 2-1 | Non-leached | Untreated Control | 5 | a | 4.9 | a |
| 2-2 | Non-leached | C8 only | 4.8 | a | 4.2 | a |
| 2-3 | Non-leached | DOT only | 2.8 | b | 2.8 | b |
| 2-4 | Non-leached | DOT, 4 hr dry, C8 | 0 | d | 0 | d |
| 2-5 | Non-leached | DOT + C8 combo | 0.8 | c, d | 0.8 | d, e |
| 2-6 | Leached | C8 only | 2.4 | b | 1.9 | b, c |
| 2-7 | Leached | DOT only | 1.9 | b, c | 1.2 | d, e |
| 2-8 | Leached | DOT, 4 hr dry, C8 | 0.7 | c, d | 0.5 | d, e |
| 2-9 | Leached | DOT + C8 combo | 1.6 | b, c | 1.2 | c, d |

*FPLSD: Fisher's Protected Least Significant Difference Ratings values with the same letters are not significant at P < 0.05

Example 3

A C8 stock formulation was prepared containing 50% C8/20% PE 1198/10% L-tactic acid/20% mineral oil. DOT solutions were prepared containing DOT (0.25%, v/v) in water and DOT (2.00%, v/v) in water. Carrier solutions included water and the two DOT solutions. Test solutions were prepared with the C8 stock formulation (6% v/v) in water and in the two DOT solutions. Six groups of southern yellow pine stakes (12 replicates) were dip-treated (30 seconds) with treatments 3-1 through 3-6, inoculated with mold spores, incubated, and examined after 12 weeks (Table 3). The moldicide ratings provided in Table 3 were based on ratings wherein ratings of 1, 2, 3, 4 and 5 represented 20, 40, 60, 80 and 100% infection, respectively. The DOT treatments (3-5, 3-6), relative to the water, control (3-1), had no moldicide activity. Because the combination of DOT and the C8 treatments (3-3, 3-4) had better control than the C8 formulation, alone, (3-2) a synergy between C8 formulation and DOT was evident.

TABLE 3

Moldicide Assay

| Treatment | Formulation | Carrier Solution | Rating (12 weeks) | *FPLSD, P @ 0.05 |
|---|---|---|---|---|
| 3-1 | Water, control | water | 3 | b |
| 3-2 | C8 formulation (6%, v/v) | water | 0.83 | a |
| 3-3 | C8 formulation (6%, v/v) | DOT (0.25%, v/v) | 0.58 | a |
| 3-4 | C8 formulation (6%, v/v) | DOT (2.00%, v/v) | 0 | A |
| 3-5 | DOT (0.25%, v/v) | | 3.4 | B |
| 3-6 | DOT (2.00%, v/v) | | 3.33 | B |

*FPLSD: Fisher's Protected Least Significant Difference Ratings values with the same letters are not significant at P < 0.05

Example 4

A C8 stock formulation was prepared containing 50% C8/20% PE 1198/10% L-tactic acid/20% mineral oil. A C9 stock formulation was prepared containing 50% C9/20% PE 1198/10% L-tactic acid/20% mineral oil. A boric acid stock solution was prepared containing boric acid (0.25%, v/v) in water. Six groups of southern yellow pine stakes (12 replicates) were dip-treated (30 seconds) with treatments 4-1 through 4-6, inoculated with mold spores, incubated, and examined after 12 weeks. The moldicide ratings provided in Table 4 were based on ratings wherein ratings of 1, 2, 3, 4 and 5 represented 20, 40, 60, 80 and 100% infection, respectively.

The boric acid treatment (4-6), alone, relative to the water control (4-1), had no moldicide activity. Because C8 and C9 formulations (4-2, 4-4), alone, had less moldicide activity than the combination of boric acid and C8 (or C9) formulations (4-3, 4-5), a synergy between C8 (C9) and boric acid was demonstrated. Therefore, DOT (Table 3) or boric acid (Table 4), as carrier solutions, appeared to be beneficial over water. Boric acid or DOT, alone, had no moldicide activity at 12 weeks. The data shows improvement of fatty acid-based moldicide activity by inclusion of a borate and the combination is synergistic.

TABLE 4

Moldicide Assay

| Treatment | Composition | Carrier Solution | Rating (at 12 weeks) | *FPLSD, P @ 0.05, |
|---|---|---|---|---|
| 4-1 | water, control | water | 3.5 | A |
| 4-2 | C8 formulation (6%, v/v) | water | 0.9 | B |
| 4-3 | C8 formulation (6%, v/v) | boric acid (0.25%, v/v) | 0.33 | B |
| 4-4 | C9 formulation (6%, v/v) | water | 0.8 | B |
| 4-5 | C9 formulation (6%, v/v) | boric acid (0.25%, v/v) | 0.33 | B |
| 4-6 | boric acid (0.25%, v/v) | | 3.91 | A |

*FPLSD: Fisher's Protected Least Significant Difference Ratings values with the same letters are not significant at P < 0.05

Example 5

A first stock formulation was prepared containing 62.31% C9, 10% PE 1198, 4.5% boric acid, 2% Cu gluconate, 3.2% water, and 18% glycerol. A second stock formulation was prepared containing 50% C8, 1.41% Columbus unmodified lecithin #750, 4.5% boric acid, 2% Cu gluconate, 3.2% water, 0.89% sodium dodecyl sulfate, and 38% glycerol. A third stock formulation was prepared containing 55% C8, 15% PE 1198, 15% 6915, 1.5% boric acid, 6% glycerol, and 7.5% mineral oil. Aqueous treatment formulations were prepared (stock formulation=12%, v/v) by diluting the three formulations with water. Replicate sets of 12 southern yellow pine stakes/treatment group were subjected to a vacuum treatment and drained. A control set of 12 stakes (Table 5, 5-7) was similarly vacuum treated with water, instead of a diluted stock formulation (treatments 5-1 to 5-6). Test samples associated with treatments 5-1 through 5-3 were leached prior to exposure to mold infection, whereas the test samples associated with treatments 5-4 to 5-7, were not leached. Leaching involved contact with distilled water, with periodic changes of the water, for a period of two weeks (American Wood Protection Association. 2009, Standard AWPA E11-06).

After the stakes had been exposed to mold infection for 12 weeks, the condition of each stake was evaluated and an average rating provided. The moldicide ratings provided in Table 5 were based on ratings wherein ratings of 1, 2, 3, 4 and 5 represented 20, 40, 60, 80 and 100% infection, respectively. Relative to the water control (5-7) and non-leached, treated blocks (5-4 to 5-6), moldicide activities for the leached blocks (5-1 to 5-3) were maintained and not lost after leaching.

F-2 formulation (6%, v/v), All reduced pressure treatments were for 30 minutes. The stakes in treatments 6-1 and 6-2 were leached by placing the stakes in distilled water for two weeks with periodic replacement with fresh distilled water. The stakes in treatments 6-3, 6-4 and 6-5 were not leached. After treatment, stakes were inoculated with spores from a mold consortium, incubated for 12 weeks and then evaluated for presence of mold infection. The moldicide ratings provided in Table 6 were based on ratings wherein ratings of 1, 2, 3, 4 and 5 represented 20, 40, 60, 80 and 100% infection, respectively.

Because moldicide activity for each treatment was essentially the same for leached and unleached stakes, sufficient formulation ingredients were retained and not lost from treated stakes during exposure to water. Specifically, vacuum treatments of borate/fatty acid (treatments 6-2, 6-4) showed that a DOT pretreatment, followed by air drying and then application of a C8 formulation completely controlled mold growth at 12 weeks, for both leached and un-leached samples. Combining C8 and boric acid in a single formulation (treatments 6-1, 6-3) also had excellent control for both leached and un-leached blocks, Formulation dilutions in water (treatment solutions) were homogeneous and stable.

TABLE 5

Moldicide Assay

| Test # | Leached/Non-Leached | Treatment | Rating 12 weeks | *FPLSD, P @ 0.05, |
|---|---|---|---|---|
| 5-1 | Leached | 12% (62.31% C9/10% PE 1198/4.5% boric acid/2% Cu gluconate/3.2% water/18% glycerol), vacuum treat, drain/dry (overnight) | 0.5 | a |
| 5-2 | Leached | 12% (50% C8/1.41% #750/4.5% boric acid/2% Cu gluconate/3.2% water/0.89% SDS/38% glycerol), vacuum treat, drain/dry (overnight) | 0.16 | a |
| 5-3 | Leached | 12% (55% C8/15% PE 1198/15% 6915/1.5% boric acid/6% glycerol/7.5% mineral oil), vacuum treat, drain/dry (overnight) | 0 | a |
| 5-4 | Non-leached | 12% (62.31% C9/10% PE 1198/4.5% boric acid; 2% Cu gluconate/3.2% water/18% glycerol), vacuum treat, drain/dry (overnight) | 0.58 | a |
| 5-5 | Non-leached | 12% (50% C8/1.41% #750/4.5% boric acid/2% Cu gluconate/3.2% water/0.89% SDS/38% glycerol), vacuum treat, drain/dry (overnight) | 0 | a |
| 5-6 | Non-leached | 12% (55% C8/15% PE 1198/15% 6915/1.5% boric acid/6% glycerol/7.5% mineral oil), vacuum treat, drain/dry (overnight) | 0 | a |
| 5-7 | Non-leached | water control | 2.25 | b |

*FPLSD: Fisher's Protected Least Significant Difference Ratings values with the same letters are not significant at P < 0.05

Example 6

Three stock treatment formulations were prepared. The first formulation (F-1) contained 60% C8, 20% PE1198, 15% mineral oil, 1% boric acid, 4% glycerol. The second formulation (F-2) contained 50% C8, 20% PE 1198, 10% L-lactic acid (88%), and 20% mineral oil. The third formulation (F-3) contained DOT (5%, g/v) in water. Formulation F-3 was used without further dilution. A 12% (v/v) formulation based on F-1 was prepared by dilution with water. A 6% (v/v) formulation based on F-2 was prepared. The treatment for 6-5 (control) was water (Table 6). Twelve replicate southern yellow pine stakes were used for each treatment group. For treatment 6-1 and 6-3, the 12%, v/v, solution of 17-1 was used at reduced pressure. For treatment 6-2 and 6-4, stakes were first treated at reduced pressure with F-3, air dried for 30 minutes and then further treated at reduced pressure with the

TABLE 6

Moldicide Assay

| Treatment | Formulation | Leached/Un-leached | Rating (12 weeks) | *FPLSD P @ 0.05, |
|---|---|---|---|---|
| 6-1 | 12% F-1 [60% C8/20% PE1198/15% mineral oil/5% boric acid, glycerol (20% boric acid:80% glycerol)] | Leached | 0.1 | a |
| 6-2 | F-3 [5% DOT] followed by 6% F-2 [50% C8/20% PE 1198/10% L-lactic acid (88%)/20% mineral oil] | Leached | 0 | a |
| 6-3 | 12% F-1 [60% C8/20% PE1198/15% mineral oil/5% boric acid, glycerol | Un-leached | 0 | a |

TABLE 6-continued

Moldicide Assay

| Treatment | Formulation | Leached/Un-leached | Rating (12 weeks) | *FPLSD P @ 0.05 |
|---|---|---|---|---|
| | (20% boric acid:80% glycerol)] | | | |
| 6-4 | F-3 [5% DOT] followed by 6% F-2 [50% C8/20% PE 1198/10% L-lactic acid (88%)/20% mineral oil] | Un-lactic acid | 0 | a |
| 6-5 | water, control | Un-leached | 3.1 | b |

*FPLSD: Fisher's Protected Least Significant Difference Ratings values with the same letters are not significant at P < 0.05

Example 7

Three stock formulations were prepared. The first stock formulation contained 50% C8, 14.8% mineral oil, 10% PE 1198, 10% 6915, 2% boric acid, 8% glycerol, 2.0% Cu gluconate and 3.2% water. The second stock formulation contained 50% C8/C10 mixture (60:40), 20% PE 1198, and 30% mineral oil. The third stock formulation contained 50% C8, 20% PE 1198; and 30% mineral oil. As noted in Table 7, test formulations (6% and 12%) were made by diluting the stock formulations with water. Twelve replicates of southern yellow pine stakes were treated with each test formulation (7-1 through 7-12) and the water, control (7-13) at reduced pressure (room temperature). The stakes from test 7-1 through 7-6 were leached by placing the stakes in distilled water for two weeks with periodic replacement with fresh distilled water. The stakes in treatments 7-7 through 7-12 were not leached. After full treatment the stakes were exposed to mold infection for 8 weeks and evaluated. The moldicide ratings provided in Table 7 were based on ratings wherein ratings of 1, 2, 3, 4 and 5 represented 20, 40, 60, 80 and 100% infection, respectively.

Overall, based on good mold protection in leached stakes (7-1 to 7-6), essentially all or nearly all fatty acid based formulations (including treatments 7-1, 7-2, containing boric acid), were retained after extensive leaching with water.

TABLE 7

Moldicide Assay

| Test | Formulation | Leached/Non-Leached | Rate (%, v/v) | Average Rating (8 weeks) |
|---|---|---|---|---|
| 7-1 | 50% C8/14.8% mineral oil/10% PE 1198/10% 6915/2% boric acid/8% glycerol/2.0% Cu gluconate/3.2% water | Leached | 6 | 1.5 |
| 7-2 | 50% C8/14.8% mineral oil/10% PE 1198/10% 6915/2% boric acid/8% glycerol/2.0% Cu gluconate/3.2% water | Leached | 12 | 0.08 |
| 7-3 | 50% C8, C10/20% PE 1198/30% mineral oil | Leached | 6 | 0.16 |
| 7-4 | 50% C8, C10/20% PE 1198/30% mineral oil | Leached | 12 | 0 |
| 7-5 | 50% C8/20% PE 1198/30% mineral oil | Leached | 6 | 0.08 |
| 7-6 | 50% C8/20% PE 1198/30% mineral oil | Leached | 12 | 0 |
| 7-7 | 50% C8/14.8% mineral oil/10% PE 1198/10% 6915/2% boric acid/8% glycerol/2.0% Cu gluconate/3.2% water | Non-Leached | 6 | 0.16 |

TABLE 7-continued

Moldicide Assay

| Test | Formulation | Leached/Non-Leached | Rate (%, v/v) | Average Rating (8 weeks) |
|---|---|---|---|---|
| 7-8 | 50% C8/14.8% mineral oil/10% PE 1198/10% 6915/2% boric acid/8% glycerol/2.0% Cu gluconate/3.2% water | Non-Leached | 12 | 0 |
| 7-9 | 50% C8, C10/20% PE 1198/30% mineral oil | Non-Leached | 6 | 0 |
| 7-10 | 50% C8, C10/20% PE 1198/30% mineral oil | Non-Leached | 12 | 0 |
| 7-11 | 50% C8/20% PE 1198/30% mineral oil | Non-Leached | 6 | 0 |
| 7-12 | 50% C8/20% PE 1198/30% mineral oil | Non-Leached | 12 | 0 |
| 7-13 | water, control | | | 3.25 |

Example 8

Three formulations were prepared. Formulation if contained 50% C8, 20% PE 1198, 10% L-lactic acid, and 20% mineral oil. Formulation 2 contained 50% C8, 14.8% mineral oil, 10% PE 1198, 10% 6915, 2% boric acid, 8% glycerol, 2.0% copper gluconate, and 3.2% water. Formulation 3 contained 50% C8, 10% mineral oil, 10% PE 1198, 10% 6915, 14.8% DOT, 2.0% copper gluconate, and 3.2% water. The three formulations were utilized in 4 distinct treatments. Treatment #1 involved treatment of wood blocks with an aqueous solution of DOT (5%, g/v) followed by treatment with formulation #1 (6%, v/v) diluted with water; treatment #2 involved treatment of wood blocks with formulation #1 (6%, v/v) diluted with water; treatment #3 involved treatment of wood blocks with formulation #2 (6%, v/v) diluted with water; and treatment #4 involved treatment of wood blocks with formulation #3 (6%, v/v) diluted with water. The wooden blocks were treated according to treatments #1-4 with the specified formulations at reduced pressure [26 psi (550 mm fig)] for 30 minutes.

Five replicate blocks of southern yellow pine (*G. trabeum, P. placenta*) and sweet gum (*T. versicolor*) were utilized for each treatment group and were inoculated with the designated strain of decay fungi. Tests were carried out according to Standard Method of Testing Wood Preservatives by Laboratory Soil-Block Cultures (AWPA E-10). The weight loss for each of the blocks was determined after 3 months. The results are provided below in Table 8.

TABLE 8

Control of Decay Fungi

Percent weight loss (3 months)

| | G. trabeum | | P. placenta | | T. versicolor | |
|---|---|---|---|---|---|---|
| Treatment | Average | P @ 0.05 | Average | P @ 0.05 | Average | P @ 0.05 |
| Untreated Control | 35.12 | c | 22.13 | a | 64.05 | e |
| #8-1 | 3.6 | a | 4.25 | a | 3.98 | a |
| #8-2 | 11.63 | b | 10.57 | a | 50.8 | d |
| #8-3 | 5.1 | a | 3.35 | a | 40.12 | c |
| #8-4 | 13.22 | b | 4.14 | a | 28.95 | b |

*FPLSD: Fisher's Protected Least Significant Difference Ratings values with the same letters are not significant at P < 0.05

*Gloeophyllum trabeum*-MAD617: brown rot
*Postia placenta*-MAD698: brown rot
*Trametes versicolor*-MAD697: white rot

Example 9

Three formulations were utilized in this example. The first included a mixture containing 50% of a 60:40 mixture of C8:C10 (caprylic acid: capric acid), 20% PE 1198 (PE 1198LA is a phosphate ester emulsifier available from Huntsman Chemical), and 30% mineral oil. The second formulation contained 50% of a 60:40 mixture of C8:C10, 20% PE 1198, and 20% mineral oil, and 10% of a solution containing DOT in glycerol (20% DOT, g/v in glycerol). The third formulation contained 50% of a 60:40 mixture of C8:C10, 20% PE 1198, and 30% of a solution containing DOT in glycerol (20% DOT, g/v in glycerol). Finally, a 1.00% (v/v) aqueous mixture containing the commercial wood preservative Kop-coat NP-1 was prepared. Kop-coat NP-1 is an emulsion containing didecyl dimethyl ammonium chloride and 3-iodo-2-propynyl butyl carbamate. Kop-Coat is a registered trademark of Kop-Coat, Inc. located at 436 Seventh Avenue 1850 Koppers Building Pittsburgh Pa. 15219. The first three formulations (9-2 to 9-4) were diluted with water at a dilution rate of 9% (v/v). The Kop-coat NP-1 formulation was used without further dilution. The formulations were applied to 12 replicate southern yellow pine stakes/treatment group utilizing 30 second dip treatments. The treated stakes were exposed to a mold inoculum and then evaluated at 4 weeks and at 8 weeks. Stakes treated with formulations containing fatty acids, DOT and an emulsifier (9-3 and 9-4) demonstrated better control of mold than stakes treated with a formulation containing only a fatty acid and an emulsifier (9-2) or the stakes treated with the commercial preservative (9-5).

TABLE 9

Moldicide Assay

| Test | Test Formulation | Dilution Rate (%, v/v) | Rating Average (week 4) | Rating Average (week 8) |
|---|---|---|---|---|
| 9-1 | Water, control | | 2.25 | 1.75 |
| 9-2 | 50% C8, C10/20% PE 1198LA/ 30% mineral oil | 9 | 0.75 | 0.83 |
| 9-3 | 50% C8, C10/20% PE 1198LA/ 20% mineral oil/10% glycerol, DOT | 9 | 0 | 0.08 |
| 9-4 | 50% C8, C10/20% PE 1198LA/30% glycerol, DOT | 9 | 0.5 | 0.33 |
| 9-5 | Kop-coat NP-1 | 1* | 1 | 0.92 |

*Manufacturer's Recommended Rate

Example 10

Control of Sapstain (at 12 Weeks)

Sapstain discoloration of stored lumber can be controlled more effectively using a C8/C10 formulation when combined with disodium octaborate tetrahydrate or DOT (Table 10). Whereas, a 12%, v/v, application rate of a formulation (treatment 2) is very effective, addition of DOT/glycerol further reduces mold infection and achieves complete control at 12 weeks (treatments 4, 5).

TABLE 10

Sapstain Assay

| | Treatments | Rate (v/v) | Rating |
|---|---|---|---|
| 10-1 | Water, control | | 2.25 |
| 10-2 | 50% C8, C10/20% PE 1198LA/30% mineral oil | 12% | 0.25 |
| 10-3 | 50% C8, C10/20% PE 1198LA/20% mineral oil/2% DOT/8% glycerol | 12% | 0.16 |
| 10-4 | 50% C8, C10/20% PE 1198LA/10% mineral oil/4% DOT/16% glycerol | 12% | 0 |
| 10-5 | 50% C8, C10/20% PE 1198LA/6% DOT, 24% glycerol | 12% | 0 |

12 replicate southern yellow pine stakes/treatment group
30 second dip treatments

Example 11

Control of Mold Fungi

More efficient control of mold fungi was observed when the same C8, C10 formulation (Table 10) was combined with DOT. Two application rates (3 and 12%, v/v) of each formulation were tested and ratings were recorded at 12 weeks (Table 11).

TABLE 11

Moldicide Assay

| | Treatments | Rate (% v/v) | Rating |
|---|---|---|---|
| 11-1 | Water, control | | 2 |
| 11-2 | 50% C8, C10/20% PE 1198LA/30% mineral oil | 3 | 1.33 |
| 11-3 | 50% C8, C10/20% PE 1198LA/30% mineral oil | 12 | 0.33 |
| 11-4 | 50% C8, C10/20% PE 1198LA/10% mineral oil/4% DOT/16% glycerol | 3 | 0.58 |
| 11-5 | 50% C8, C10/20% PE 1198LA/10% mineral oil/4% DOT/16% glycerol | 12 | 0.25 |

30 second dip treatments

Example 12

Control of Mold Fungi

Comparison of moldicide activity of a C9 formulation diluted into water (Table 12, treatment 2) and also diluted into a DOT solution at 1%, g/v (treatment 3) revealed that DOT increased moldicide activity. The C9 formulation had less activity when diluted in water (treatment 2). Because DOT, alone (treatment 4), had no moldicide activity, relative to the water control (treatment 1), synergy between the C9 formulation and DOT was shown.

TABLE 12

Moldicide Assay

| | Treatments* | Carrier Solution | Rating |
|---|---|---|---|
| 12-1 | Water, control | water | 2.42 |
| 12-2 | 70% C9/20% Emsorb 6915/10% PE 1198 | water | 0.42 |

TABLE 12-continued

Moldicide Assay

| Treatments* | Carrier Solution | Rating |
|---|---|---|
| 12-3 | 70% C9/20% Emsorb 6915/10% PE 1198 | DOT** | 0.08 |
| 12-4 | No fatty acid formulation | DOT** | 2.58 |

*6%, v/v, rate of C9 formulation applied
**DOT at 1%, g/v, used as carrier solution
12 replicate southern yellow pine stakes/treatment group
30 second dip treatments Example 13

Substituting DOT/glycerol for mineral oil in a C8, C10 formulation (Table 13: treatment 4) is more potent than only using mineral oil as a diluent (treatment 2). A blend of mineral oil and DOT (treatment 3) had even better moldicide activity.

TABLE 13

Moldicide Assay

| | Treatments | Rate (v/v) | Rating |
|---|---|---|---|
| 13-1 | Water, control | | 1.75 |
| 13-2 | 50% C8, C10/20% PE 1198LA/30% mineral oil | 9% | 0.83 |
| 13-3 | 50% C8, C10/20% PE 1198LA/20% mineral oil/2% DOT/8% glycerol | 9% | 0.08 |
| 13-4 | 50% C8, C10/20% PE 1198LA/6% DOT, 24% glycerol | 9% | 0.33 |

12 replicate southern yellow pine stakes/treatment group
30 second dip treatments Example 14

An adjuvant such as Hasten (methylated seed oil) can facilitate pesticide activity of a fatty acid-based formulation. Such a combination was tested using water (treatment 3), DOT (treatments 4, 5) and boric acid (treatment 6) as carrier systems (Table 14). Enhancement of the C8 formulation and Hasten (treatment 3) by DOT at 0.96 and 1.92%, g/v, and by boric acid at 0.48%, v/v, was very effective. None of the control groups (treatments 1-2, 7-10 had moldicide activity. Synergy between the C8 formulation and a borate (both DOT and boric acid) was shown.

TABLE 14

Moldicide Assay

| | Treatments | Adjuvant | Carrier | Rating (12 weeks) |
|---|---|---|---|---|
| 14-1 | Water, control | | water | 3 |
| 14-2 | Water, control | Hasten** | water | 4.75 |
| 14-3 | C8 formulation* | Hasten** | water | 1.42 |
| 14-4 | C8 formulation* | Hasten** | 0.96% DOT | 0.08 |
| 14-5 | C8 formulation* | Hasten** | 1.92% DOT | 0.5 |
| 14-6 | C8 formulation* | Hasten** | 0.48% Boric Acid | 0.58 |

TABLE 14-continued

Moldicide Assay

| | Treatments | Adjuvant | Carrier | Rating (12 weeks) |
|---|---|---|---|---|
| 14-7 | 1.92%, g/v, DOT | Hasten** | water | 3.83 |
| 14-8 | 0.48%, g/v, boric | Hasten** | water | 4.33 |
| 14-9 | 1.92%, g/v, DOT | | water | 3.83 |
| 14-10 | 0.48%, g/v, boric | | water | 4.58 |

*84.5% C8/1.41% K-EML lecithin/14.1% propionic acid (application rate of C8 formulation was 6%, v/v, in water)
**Wilbur Ellis Hasten used at 2%, v/v, application rate
12 replicate southern yellow pine stakes/treatment group
30 second dip treatments Example 15

Formulations 15-2 through 15-11 were prepared from two glycerol-based stock solutions containing 20% boric acid and 20% DOT, respectfully. The formulations illustrated in Table 15 were diluted with distilled water to provide 18% aqueous solutions for treatment. PE 1198LA is a phosphate ester emulsifier available from Huntsman Chemical. Six replicates of southern yellow pine stakes were treated with each test formulation (15-1 through 15-11) and the water, control (15-1) at reduced pressure (room temperature, 25 psi, 70 minutes). The stakes from test 15-1 through 15-1.1 were leached by placing the stakes in distilled water for two weeks with periodic replacement with fresh distilled water. After full treatment the stakes were inoculated with a three strain inoculum (*A. niger* 2.242, *P. chrysogenum* PH02, and *Trichoderma viride* 20476), incubated for 4 weeks, and evaluated. The moldicide ratings provided in Table 15 were based on ratings wherein ratings of 0, 1, 2, 3, 4 and 5 represented 0, 20, 40, 60, 80 and 100% infection, respectively. Each of the formulations provided very good mold protection in leached stakes (15-2 to 15-11),

TABLE 15

Formulations containing two Borates in Combination with Fatty Acids (3 Strain Inoculum)

| Test# | Treatments | Mold Rating* |
|---|---|---|
| 15-1 | Distilled water, control | 1 |
| 15-2 | 50% C6/20% PE 1198LA/30% BORIC, GLYCEROL | 0 |
| 15-3 | 50% C7/20% PE 1198LA/30% BORIC, GLYCEROL | 0.16 |
| 15-4 | 50% C8/20% PE 1198LA/30% BORIC, GLYCEROL | 0 |
| 15-5 | 50% C9/20% PE 1198LA/30% BORIC, GLYCEROL | 0 |
| 15-6 | 50% C8, C10/20% PE 1198LA/30% BORIC, GLYCEROL | 0 |
| 15-7 | 50% C6/20% PE 1198LA/30% DOT, GLYCEROL | 0 |
| 15-8 | 50% C7/20% PE 1198LA/30% DOT, GLYCEROL | 0 |
| 15-9 | 50% C8/20% PE 1198LA/30% DOT, GLYCEROL | 0 |
| 15-10 | 50% C9/20% PE 1198LA/30% DOT, GLYCEROL | 0 |
| 15-11 | 50% C8, C10/20% PE 1198LA/30% DOT, GLYCEROL | 0 |

*Mold ratings: 0 = no mold, 1 = 20% mold, 3 = 60% mold, 4 = 80% mold, 5 = 100% mold Example 16

Formulations 16-2 through 16-11 were prepared from two glycerol-based stock solutions containing 20% boric acid and 20% DOT, respectfully. The formulations illustrated in Table 16 were diluted with distilled water to provide 18% aqueous solutions for treatment, PE 11.98LA is a phosphate ester emulsifier available from Huntsman Chemical. Six replicates of southern yellow pine stakes were treated with each test formulation (16-1 through 16-11) and the water, control (16-1) at reduced pressure (room temperature, 25 psi, 70 minutes). The stakes from test 16-1 through 16-11 were leached by placing the stakes in distilled water for two weeks with periodic replacement with fresh distilled water. After full treatment the stakes were inoculated with a four strain inoculum (*A. niger* 2.242, *P. chrysogenum* PH02, *Trichoderma viride* 20476, and *Alternaria alternata*), incubated for 4 weeks, and evaluated. The moldicide ratings provided in Table 16 were based on ratings wherein ratings of 0, 1, 2, 3, 4 and 5 represented 0, 20, 40, 60, 80 and 100% infection, respectively. Each of the formulations provided very good mold protection in leached stakes (16-2 to 16-11).

TABLE 16

Two Borates in Combination with Fatty Acids (4 Strain Inoculum)

| Test# | Treatments | Mold Rating* |
|---|---|---|
| 16-1 | Distilled water, control | 1.16 |
| 16-2 | 50% C6/20% PE 1198LA/30% BORIC, GLYCEROL | 0 |
| 16-3 | 50% C7/20% PE 1198LA/30% BORIC, GLYCEROL | 0.16 |
| 16-4 | 50% C8/20% PE 1198LA/30% BORIC, GLYCEROL | 0 |
| 16-5 | 50% C9/20% PE 1198LA/30% BORIC, GLYCEROL | 0.16 |
| 16-6 | 50% C8, C10/20% PE 1198LA/30% BORIC, GLYCEROL | 0 |
| 16-7 | 50% C6/20% PE 1198LA/30% DOT, GLYCEROL | 0 |
| 16-8 | 50% C7/20% PE 1198LA/30% DOT, GLYCEROL | 0 |
| 16-9 | 50% C8/20% PE 1198LA/30% DOT, GLYCEROL | 0 |
| 16-10 | 50% C9/20% PE 1198LA/30% DOT, GLYCEROL | 0 |
| 16-11 | 50% C8, C10/20% PE 1198LA/30% DOT, GLYCEROL | 0.16 |

*Mold ratings: 0 = no mold, 1 = 20% mold, 3 = 60% mold, 4 = 80% mold, 5 = 100% mold Example 17

Formulations 17-2 through 17-4 were prepared from two glycerol-based solutions containing 20% boric acid and 20% DOT. The formulations illustrated in Table 17 were diluted with distilled water to provide 18% aqueous solutions for treatment. PE 1198LA is a phosphate ester emulsifier available from Huntsman Chemical. Twelve replicates of southern yellow pine stakes were treated with each test formulation (17-2 through 17-4) and the water, control (17-1) at reduced pressure (room temperature, 25 psi, 70 minutes). The stakes from test 17-1 through 17-4 were leached by placing the stakes in distilled water for two weeks with periodic replacement with fresh distilled water. After full treatment the stakes were inoculated with a four strain inoculum (*A. niger* 2.242, *P. chrysogenum* PH02, *Trichoderma viride* 20476, and *Alternaria alternata*), the moldicide ratings were determined at 4 weeks, 8 weeks, and 12 weeks and the results are provided in Table 17. Evaluation provided a rating of 0, 1, 2, 3, 4 and 5 for a resulting 0, 20, 40, 60, 80 and 100% infection, respectively. Each of the formulations provided very good mold protection in leached stakes (17-2 to 17-4).

TABLE 17

Two Borates in Combination with C8 and C9 Fatty Acids (4 Strain Inoculum)

| | | Mold Rating (Average)* | | |
|---|---|---|---|---|
| Test# | Treatments | 4 wk | 8 wk | 12 wk |
| 17-1 | Control, water | 3.44 | 3 | 3.44 |
| 17-2 | 50% C9/20% PE 1198LA/30% BORIC-GLYCEROL | 0.11 | 0.33 | 0.11 |
| 17-3 | 60% C8/20% PE 1198LA/30% MINERAL OIL/2% BORIC/8%, GLYCEROL | 0 | 0 | 0 |
| 17-4 | 50% C9/20% PE 1198LA/30% DOT-GLYCEROL | 0.11 | 0.16 | 0.11 |

*Mold ratings: 0 = no mold, 1 = 20% mold, 3 = 60% mold, 4 = 80% mold, 5 = 100% mold Example 18

Formulations 18-2 through 18-7 were prepared from two glycerol-based stock solutions containing 20% boric acid. The formulations illustrated in Table 18 were diluted with distilled water to provide 6, 12, and 18% aqueous solutions for treatment. C8 and C9 formulations, including the same concentrations of PE 11198LA and boric/glycerol, were compared. PE 1198LA is a phosphate ester emulsifier available from Huntsman Chemical. Twelve replicates of southern yellow pine stakes were treated with each test formulation (18-2 through 18-7) and the water, control (18-1) at reduced pressure (room temperature, 25 psi, 70 minutes). After full treatment the stakes were inoculated with a four strain inoculum (*A. niger* 2.242, *P. chrysogenum* PH02, *Trichoderma viride* 20476, and *Alternaria alternata*) and incubated. Stakes were evaluated at 4 weeks, 8 weeks, and at 12 weeks to provide the moldicide ratings in Table 18. Evaluation provided a rating of 0, 1, 2, 3, 4 and 5 for a resulting 0, 20, 40, 60, 80 and 100% infection, respectively. Each of the formulations provided very good mold protection in leached stakes (18-2 to 18-7).

TABLE 18

C8 and C9 formulations with Boric Acid at 3 Application Rates (4 Strain Inoculum)

| | | | Mold Rating (average)* | | |
|---|---|---|---|---|---|
| Test# | Vacuum Treatments | Rate (v/v) | 4 wk Avg | 8 wk Avg | 12 wk Avg |
| 18-1 | Water, control | | 3 | 3.75 | 3.92 |
| 18-2 | 50% C9/20% PE 1198LA/30% BORIC-GLYCEROL | 6 | 0 | 0 | 0 |
| 18-3 | 50% C9/20% PE 1198LA/30% BORIC-GLYCEROL | 12 | 0 | 0 | 0 |
| 18-4 | 50% C9/20% PE 1198LA/30% BORIC, GLYCEROL | 18 | 0 | 0 | 0 |
| 18-5 | 50% C8/20% PE 1198LA/30% BORIC, GLYCEROL | 6 | 0 | 0 | 0 |
| 18-6 | 50% C8/20% PE 1198LA/30% BORIC, GLYCEROL | 12 | 0 | 0 | 0.08 |
| 18-7 | 50% C8/20% PE 1198LA/30% BORIC, GLYCEROL | 18 | 0 | 0 | 0 |

*Mold ratings: 0 = no mold, 1 = 20% mold, 3 = 60% mold, 4 = 80% mold, 5 = 100% mold Example 19

Formulations 19-2 through 19-11 were prepared from two glycerol-based stock solutions containing 20% boric acid and 20% DOT, respectfully. PE 1198LA is a phosphate ester emulsifier available from Huntsman Chemical. Six replicates of southern yellow pine stakes (19-1 through 19-11) were given a 30 second dip treatment in a formulation at room temperature. After fill treatment the stakes were inoculated with a four strain inoculum (*A. niger* 2.242, *P. chrysogenum* PH02, *Trichoderma viride* 20476, and *Alternaria alternata*), incubated. Stakes were evaluated at 4 weeks and at 8 weeks to provide the moldicide ratings reproduced in Table 19. Evaluation provided a rating of 0, 1, 2, 3, 4 and 5 for a resulting 0, 20, 40, 60, 80 and 100% infection, respectively. Each of the formulations provided good to very good mold protection in treated stakes (19-2 to 19-11),

TABLE 19

Formulations of Fatty Acids with Borates Utilizing Dip Treatment (4 Strain Inoculum)

| Test# | Treatments | Mold Rating (Avg)* | |
|---|---|---|---|
| | | 4 wk | 8 wk |
| 19-1 | Distilled water, control | 2.16 | 2.83 |
| 19-2 | 50% C6/20% PE 1198LA/30% BORIC, GLYCEROL | 0 | 0 |
| 19-3 | 50% C7/20% PE 1198LA/30% BORIC, GLYCEROL | 0 | 0 |
| 19-4 | 50% C8/20% PE 1198LA/30% BORIC, GLYCEROL | 0 | 0 |
| 19-5 | 50% C9/20% PE 1198LA/30% BORIC, GLYCEROL | 0 | 0.5 |
| 19-6 | 50% C8, C10/20% PE 1198LA/30% BORIC, GLYCEROL | 0.16 | 0.75 |
| 19-7 | 50% C6/20% PE 1198LA/30% DOT, GLYCEROL | 0.16 | 0.16 |
| 19-8 | 50% C7/20% PE 1198LA/30% DOT, GLYCEROL | 0 | 0 |
| 19-9 | 50% C8/20% PE 1198LA/30% DOT, GLYCEROL | 0 | 0 |
| 19-10 | 50% C9/20% PE 1198LA/30% DOT, GLYCEROL | 0 | 0 |
| 19-11 | 50% C8, C10/20% PE 1198LA/30% DOT, GLYCEROL | 0 | 0.16 |

*Mold ratings: 0 = no mold, 1 = 20% mold, 3 = 60% mold, 4 = 80% mold, 5 = 100% mold Example 20

Formulations 20-2 through 20-111 were prepared from two glycerol-based stock solutions containing 20% boric acid and 20% DOT, respectfully. PE 1198 LA, is a phosphate ester emulsifier available from Huntsman Chemical. Six replicates of southern yellow pine stakes (20-1 through 20-1) were given 30 second dip treatments in a formulation at room temperature. After full treatment the stakes were inoculated with a three strain inoculum (*A. niger* 2.242, *P. chrysogenum* PH02, and *Trichoderma viride* 20476) and incubated. Stakes were evaluated at 4 weeks and at 8 weeks to provide the moldicide ratings reproduced in Table 20. Evaluation provided a rating of 0, 1, 2, 3, 4 and 5 for a resulting 0, 20, 40, 60, 80 and 100% infection, respectively. Overall, the formulations provided improved mold protection in treated stakes (20-2 to 20-11).

TABLE 20

Formulations of Fatty Acids with Borates Utilizing Dip Treatment (3 Strain Inoculum)

| Test# | Treatments | Mold Rating (Avg)* | |
|---|---|---|---|
| | | 4 wk | 8 wk |
| 20-1 | Distilled water, control | 3.16 | 3.66 |
| 20-2 | 50% C6/20% PE 1198LA/30% BORIC, GLYCEROL | 0 | 0 |

TABLE 20-continued

Formulations of Fatty Acids with Borates Utilizing Dip Treatment (3 Strain Inoculum)

| Test# | Treatments | Mold Rating (Avg)* | |
|---|---|---|---|
| | | 4 wk | 8 wk |
| 20-3 | 50% C7/20% PE 1198LA/30% BORIC, GLYCEROL | 0 | 0 |
| 20-4 | 50% C8/20% PE 1198LA/30% BORIC, GLYCEROL | 0 | 1.16 |
| 20-5 | 50% C9/20% PE 1198LA/30% BORIC, GLYCEROL | 0 | 0.83 |
| 20-6 | 50% C8, C10/20% PE 1198LA/30% BORIC, GLYCEROL | 1 | 0.66 |
| 20-7 | 50% C6/20% PE 1198LA/30% DOT, GLYCEROL | 0 | 0 |
| 20-8 | 50% C7/20% PE 1198LA/30% DOT, GLYCEROL | 0 | 0.16 |
| 20-9 | 50% C8/20% PE 1198LA/30% DOT, GLYCEROL | 0 | 0 |
| 20-10 | 50% C9/20% PE 1198LA/30% DOT, GLYCEROL | 0 | 0.16 |
| 20-11 | 50% C8, C10/20% PE 1198LA/30% DOT, GLYCEROL | 0 | 0 |

*Mold ratings: 0 = no mold, 1 = 20% mold, 3 = 60% mold, 4 = 80% mold, 5 = 100% mold Example 21

Formulations 21-2 through 21-11 were prepared from two glycerol-based stock solutions containing 20% boric acid and 20% DOT, respectfully. The formulations illustrated in Table 21 were diluted with distilled water to provide 18% aqueous solutions for treatment, PE 11.98LA is a phosphate ester emulsifier available from Huntsman Chemical. Twelve replicates of southern yellow pine stakes were treated with each test formulation (21-2 through 21-11) and the water, control (22-1) at reduced pressure (room temperature, 25 psi, 70 minutes). The stakes from test 21-1 through 21-11 were leached by placing the stakes in distilled water for two weeks with periodic replacement with fresh distilled water. After full treatment the stakes were inoculated with a four strain inoculum (*A. niger* 2.242, *P. chrysogenum* PH02, *Trichoderma viride* 20476, and *Alternaria alternata*), incubated and evaluated at 4 weeks, 8 weeks, and at 12 weeks. The moldicide ratings provided in Table 21 were based on ratings wherein ratings of 0, 1, 2, 3, 4 and 5 represented 0, 20, 40, 60, 80 and 100% infection, respectively. Selected formulations, particularly 21-8 through 21-11 provided good mold protection in leached stakes (21-2 to 21-11).

TABLE 21

Formulations of Fatty Acids with Borates at 3 Months (4 Strain Inoculum)

| Test# | Treatments | Mold Rating (Avg)* | | |
|---|---|---|---|---|
| | | 4 wk | 8 wk | 12 wk |
| 21-1 | Distilled water, control | 1.16 | 2 | 2.5 |
| 21-2 | 50% C6/20% PE 1198LA/30% BORIC, GLYCEROL | 0.16 | 0.66 | 2.6 |
| 21-3 | 50% C7/20% PE 1198LA/30% BORIC, GLYCEROL | 0 | 0 | 0.16 |
| 21-4 | 50% C8/20% PE 1198LA/30% BORIC, GLYCEROL | 0.16 | 0.16 | 1 |
| 21-5 | 50% C9/20% PE 1198LA/30% BORIC, GLYCEROL | 0 | 0 | 0.5 |
| 21-6 | 50% C8, C10/20% PE 1198LA/30% BORIC, GLYCEROL | 0 | 0.16 | 1.66 |

TABLE 21-continued

Formulations of Fatty Acids with Borates at 3 Months
(4 Strain Inoculum)

| | | Mold Rating (Avg)* | | |
|---|---|---|---|---|
| Test# | Treatments | 4 wk | 8 wk | 12 wk |
| 21-7 | 50% C6/20% PE 1198LA/30% DOT, GLYCEROL | 0 | 0 | 1.33 |
| 21-8 | 50% C7/20% PE 1198LA/30% DOT, GLYCEROL | 0 | 0 | 0 |
| 21-9 | 50% C8/20% PE 1198LA/30% DOT, GLYCEROL | 0 | 0 | 0 |
| 21-10 | 50% C9/20% PE 1198LA/30% DOT, GLYCEROL | 0 | 0 | 0 |
| 21-11 | 50% C8, C10/20% PE 1198LA/30% DOT, GLYCEROL | 0 | 0 | 0 |

*Mold ratings: 0 = no mold, 1 = 20% mold, 3 = 60% mold, 4 = 80% mold, 5 = 100% mold

Example 22

Formulations 22-2 through 22-11 were prepared from two glycerol-based stock solutions containing 20% boric acid and 20% DOT, respectfully. The formulations illustrated in Table 22 were diluted with distilled water to provide 18% aqueous solutions for treatment PE 1198LA is a phosphate ester emulsifier available from Huntsman Chemical. Twelve replicates of southern yellow pine stakes were treated with each test formulation (22-2 through 22-11) and the water, control (22-1) at reduced pressure (room temperature, 25 psi, 70 minutes). The stakes from test 21-1 through 21-11 were leached by placing the stakes in distilled water for two weeks with periodic replacement with fresh distilled water. After full treatment the stakes were inoculated with a three strain inoculum (*A. niger* 2.242, *P. chrysogenum* PH02, and *Trichoderma viride* 20476), incubated and evaluated at 4 weeks, 8 weeks, and at 12 weeks. The moldicide ratings provided in Table 22 were based on ratings wherein ratings of 0, 1, 2, 3, 4 and 5 represented 0, 20, 40, 60, 80 and 100% infection, respectively. Each of the formulations provided good mold protection in leached stakes (22-3 to 22-11) at 4 and 8 weeks. However, treatments 22-5, and 22-8 through 22-10 were quite effective at 12 weeks.

TABLE 22

Formulations of Fatty Acids with Borates at 3 Months
(3 Strain Inoculum)

| | | Mold Rating(Avg)* | | |
|---|---|---|---|---|
| Test# | Treatments | 4 wk | 8 wk | 12 wk |
| 22-1 | Distilled water, control | 1 | 2.5 | 2.66 |
| 22-2 | 50% C6/20% PE 1198LA/30% BORIC, GLYCEROL | 0.83 | 3 | 3.66 |
| 22-3 | 50% C7/20% PE 1198LA/30% BORIC, GLYCEROL | 0.16 | 0.5 | 2.33 |
| 22-4 | 50% C8/20% PE 1198LA/30% BORIC, GLYCEROL | 0 | 0 | 1 |
| 22-5 | 50% C9/20% PE 1198LA/30% BORIC, GLYCEROL | 0 | 0 | 0.16 |
| 22-6 | 50% C8, C10/20% PE 1198LA/30% BORIC, GLYCEROL | 0.16 | 0.66 | 1.33 |
| 22-7 | 50% C6/20% PE 1198LA/30% DOT, GLYCEROL | 0.16 | 0.16 | 1.33 |
| 22-8 | 50% C7/20% PE 1198LA/30% DOT, GLYCEROL | 0 | 0 | 0 |
| 22-9 | 50% C8/20% PE 1198LA/30% DOT, GLYCEROL | 0 | 0 | 0 |
| 22-10 | 50% C9/20% PE 1198LA/30% DOT, GLYCEROL | 0 | 0 | 0 |
| 22-11 | 50% C8, C10/20% PE 1198LA/30% DOT, GLYCEROL | 0 | 0 | 0.32 |

*Mold ratings: 0 = no mold, 1 = 20% mold, 3 = 60% mold, 4 = 80% mold, 5 = 100% mold

Example 23

Formulations 23-2, 23-4 through 23-6 were prepared from a 20% boric acid solution in glycerol (80%). PE 1198LA is a phosphate ester emulsifier available from Huntsman Chemical. Twelve replicates of southern yellow pine stakes were treated with each test formulation (23-2 through 23-6) and the water, control (23-1) at reduced pressure (room temperature, 25 psi, 70 minutes). The stakes from test 23-1 through 23-6 were leached by placing the stakes in distilled water for two weeks with periodic replacement with fresh distilled water. After full treatment the stakes were inoculated with a four strain inoculum (*A. niger* 2.242, *P. chrysogenum* PH02, *Trichoderma viride* 20476, and *Alternaria alternata*), incubated and evaluated at 4 weeks, 8 weeks, and at 12 weeks. The moldicide ratings provided in Table 23 were based on ratings wherein ratings of 0, 1, 2, 3, 4 and 5 represented 0, 20, 40, 60, 80 and 100% infection, respectively. Each of the formulations provided mold protection in leached stakes (23-2 to 23-5) at weeks 4 and 8. Treatment 23-2 showed complete control at 4, 8 and 12 weeks.

TABLE 23

Formulations of Fatty Acids with Boric Acid and/or Mineral Oil
(4 Strain Inoculum)

| | | Mold Rating(Avg)* | | |
|---|---|---|---|---|
| Test# | Treatments | 4 wk | 8 wk | 12 wk |
| 23-1 | Water, control | 2.08 | 4.11 | 3.3 |
| 23-2 | 60% C8/20% PE 1198LA/10% MO/10% BORIC-GLYCEROL | 0 | 0 | 0 |
| 23-3 | 34.15% C8/29.27% MO/14.63% water/14.63% PE 1198LA/7.32% 6915 | 0 | 0.33 | 1.3 |
| 23-4 | 40% C6/15% 6915/15% PE 1198LA/20% MO/10% BORIC-GLYCEROL | 0 | 0 | 0.77 |
| 23-5 | 40% C8/15% 6915/15% PE 1198LA/20% MO/10% BORIC-GLYCEROL | 0 | 0 | 0.22 |
| 23-6 | 40% C9/15% 6915/15% PE 1198LA/20% MO/10% BORIC-GLYCEROL | 0 | 1.22 | 2.33 |

*Mold ratings: 0 = no mold, 1 = 20% mold, 3 = 60% mold, 4 = 80% mold, 5 = 100% mold

Example 24

Southern Yellow Pine blocks were pressure treated with water (24-1) and the remaining formulations illustrated in Table 24 (24-2 through 24-6) according to AWPA T1-07 (Processing and Treatment Standard, 2007), Groups of five replicate blocks were each treated with water and the remaining five formulations. Blocks treated with test formulations 24-2 and 24-3 were leached with water according to the procedure provided in Standard Leach trial: (E11-06, AWPA, 2009). The remaining wood blocks were not leached. Following the treatments indicated, the blocks were subjected to a no-choice test against termites (*AWPA Standard E*1-09, 2009), The test results are illustrated below Table 24. The test results illustrated below in Table 24 illustrate that both the C8 (24-2) and the C8-C10 combination (24-3) provided a 4 to 5 fold reduction in wood loss, even after leaching. In addition, the C7 (24-4), C8 (24-5), and C9 (24-6) formulations in un-leached blocks provided a 15 to 38 fold reduction in wood toss. Untreated or control blocks (24-1) provided suffered the loss of more than 75% of the block.

TABLE 24

Control of Termite Consumption of Southern Yellow Pine

| Test # | Treatments | Rate (v/v) in water | Water Leaching after Block Treatment | Wood Digest (%)* |
|---|---|---|---|---|
| 24-1 | Water, control | | No | 77 |
| 24-2 | 50% C8/20% PE1198LA/6% DOT/24% glycerol | 18% | Yes | 14 |
| 24-3 | 50% C8, C10/20% PE1198LA/6% DOT/24% glycerol | 18% | Yes | 17 |
| 24-4 | 80% C7/20% PE1198LA | 18% | No | 5 |
| 24-5 | 80% C8/20% PE1198LA | 18% | No | 4 |
| 24-6 | 80% C9/20% PE1198LA | 18% | No | 2 |

*Blocks were evaluated at 16 days after onset of termite incubation of the southern yellow pine blocks.

DOT is disodium octaborate tetrahydrate. PE1198LA is a phosphate ester emulsifier available from Huntsman Chemical Company.

While applicants disclosure has been provided with reference to specific embodiments above, it will be understood that modifications and alterations in the embodiments disclosed may be made by those practiced in the art without departing from the spirit and scope of the invention, All such modifications and alterations are intended to be covered. All publications, patents, and patent applications cited in this specification are herein incorporated by reference as if each individual publication, patent, or patent application was specifically and individually indicated to be incorporated by reference and set forth in its entirety herein.

The invention claimed is:

1. A composition for wood treatment comprising a borate, a fatty acid, or a salt thereof wherein the fatty acid has between 5 and 22 carbon atoms and the composition is adapted to provide an emulsion when mixed with water and to protect wood treated with the composition against insects, decay fungi, and mold fungi in interior and exterior applications.

2. The composition of claim 1, wherein the composition resists leaching from treated wood upon repeated exposure to water.

3. The composition of claim 1 wherein the ratio of borate compound to fatty acid ranges from about 1:25 to about 10:1.

4. The composition of claim 3, wherein the ratio of borate compound to fatty acid ranges from about 1:15 to about 8:1.

5. The composition of claim 1, wherein the fatty acid is a carboxylic acid having from 6 to 12 carbon atoms.

6. The composition of claim 1, wherein the fatty acid is selected from the group consisting of caprylic acid, capric acid, hexanoic acid, heptanoic acid, pelargonic acid, and a combination thereof.

7. The composition of claim 1, wherein the borate compound is selected from the group consisting of disodium octaborate tetrahydrate (DOT), boric acid, a boronic acid, and a combination thereof.

8. The composition of claim 7, wherein the fatty acid is selected from the group consisting of caprylic acid, capric acid, hexanoic acid, heptanoic acid, pelargonic acid, and a combination thereof.

9. A wood-based article or structure treated with an emulstion containing a borate compound and a fatty acid having 5 to 22 carbons, and an emulsifier, the wood based article or structure capable of resisting attack by insects, decay fungi, and mold fungi.

10. The wood-based article of claim 9 wherein the borate compound and the fatty acid resist leaching when the wood-based article is subject to repeated exposures to water.

11. The wood-based article or structure of claim 9, wherein the borate compound is selected from the group consisting of DOT, boric acid and a boronic acid, wherein the treated article is capable of resisting attack by insects, decay fungi, and mold fungi in interior and exterior applications.

12. The wood-based article or structure of claim 11, wherein the fatty acid is selected from the group including caprylic acid, capric acid, pelargonic acid, and a combination thereof.

13. A composition for preserving a wood based article or structure comprising a fatty acid, sorbic acid and an emulsifier.

14. The composition of claim 13 wherein the composition resists leaching when the wood-based article or structure is subject to repeated exposures to water.

15. The composition of claim 13, further including a borate.

16. The composition of claim 15, wherein the borate is selected from the group consisting of DOT, boric acid and a boronic acid.

* * * * *